United States Patent [19]

Scanlon

[11] Patent Number: 5,989,908
[45] Date of Patent: Nov. 23, 1999

[54] MODULATION OF DRUG AND RADIATION RESISTANT GENES

[75] Inventor: Kevin J. Scanlon, Pasadena, Calif.

[73] Assignee: City of Hope, Duarte, Calif.

[21] Appl. No.: 08/793,878

[22] PCT Filed: Sep. 12, 1994

[86] PCT No.: PCT/US94/10215

§ 371 Date: May 23, 1997

§ 102(e) Date: May 23, 1997

[87] PCT Pub. No.: WO96/08558

PCT Pub. Date: Mar. 21, 1996

[51] Int. Cl.$^6$ ............................ C12N 15/85; C07H 21/04; C12Q 1/68
[52] U.S. Cl. ............................ 435/325; 435/6; 435/91.31; 435/320.1; 435/366; 435/375; 536/23.1; 536/23.2; 536/24.31; 536/24.5
[58] Field of Search .................................. 514/44; 435/6, 435/91.31, 172.3, 320.1, 325, 366; 536/24.5, 23.2

[56] References Cited

PUBLICATIONS

Holm, P.S. et al. (1994). Br. J. Cancer 70:239–243.
Toshide et al. Advan. Enzyme Regul. 32: 195–209 (1992).
Kashani–Sabet et al. Cancer Gene Therapy 1(4):V–70:326 (1994).
Gewirtz et al. PNAS 93:3161–3163 (1996).
Rojanasakul et al. Advanced Drug Del. Reviews 18:115–131 (1996).
Stull et al. Pharm. Res. 12:465–483 (1995).
Weinberg, R.A. (1989) Cancer Res. 49:3713–3721.
Rosenberg, B. (1985) Cancer. 55:2303–2316.
Gottesman, M.M. (1993) Ann. Rev. Biochem. 62:385–427.
Ransone, L.J. & Verma, I.M. (1990) Ann. Rev. Cell Biol. 6:539–557.
Scanlon, K.J. et al. (1991) Proc. Natl. Acad. Sci. (USA) 88:10591–10595.
Boguski, M.S., McCormick F. (1993) Nature 366:643–654.
Christen, R.D. et al. (1990) J. Clin. Invest. 86:1632–1640.
Hancock, M.C. et al. (1991) Cancer Res. 51:4575–4580.
Basu, A., Lazo, J.S. (1992) Cancer Res. 52:3119–3124.
Mann, S.C. et al. (1991) Int. J. Cancer 48:866–872.
Marx (1987) Science 237:854–856 (1987).
Lee, et al. (1987) Cell 49:741–752.
McKnight (1991) Scientific American, pp. 54–64.
Abate, et al. (1990) Proc. Natl. Acad. Sci. USA 87:1032–1036 (1990).
Ransone, et al. (1989) Int. J. Cancer Supplement 4:10–21.
Kouzarides, et al. (1989) Cancer Cells 1:71–76.
Rubin, E., et al. (1992) Cancer Res. 52:878–882.
Scanlon, K.J. et al. (1988) Adv. Exp. Med. Biol. 244:127–135.
Scanlon, K.J., et al. (1989) Cancer Comm. 1:269–275.
Hollander, M.C., et al. (1989) Cancer Res. 49:1687–1692.
Scanlon, K.J., et al. (1989) Anticancer Res. 9:1301–1312.
Kastan, M.B., et al. (1991) Cancer Res. 51:6304–6311.
Kuerbitz, S.J., et al. (1992) Proc. Natl. Acad. Sci. USA 89:7491–7495.
Raycroft, L., et al. (1990) Science 249:1049–1051.
Brown, R., et al. (1993) Int. J. Cancer 55:678–684.
Wang, TS–F (1991) Ann. Rev. Biochem. 60:513–552.
Schmidt, C.J., et al. (1986) Proc. Natl. Acad. Sci. USA 83:3346–3350.
Kedar, P.S., et al. (1990) Mol. Cell. Biol. 10:3852–3856.
Sklar, M.D. (1988) Cancer Res. 48:793–797.
Niimi, S. et al. (1991) Br. J. Cancer 63:237–241.
Scanlon, K.J., et al. (1989) J. Clin. Lab. Anal. 3:323–329.
Kashani–Sabet, M., et al. (1990) Eur. J. Cancer 26:383–390.
Vanhamme, L., et al. (1987) Exp. Cell Res. 169:120–126.
Binetruy, B. et al. (1991) Nature 351:122–127.
Wang, J.C. (1985) Ann. Rev. Biochem. 54:665–697.
Liu, L.F. (1989) Ann. Rev. Biochem. 58:351–375.
Ali–Osman, F., et al. (1993) Cancer Res. 53:5663–5668.
Scanlon, K.J., et al. (1988) Proc. Natl. Acad. Sci. (USA) 85:650–653.
Kashani–Sabet, M., et al. (1992) Antisense Res. Dev. 2:3–15.
Sarver, N., et al. (1990) Science 247:1222–1225.
Kashani–Sabet, M., et al. (1990) J. Biol. Chem. 265:11285–11288.
Scanlon, K.J., et al. (1986) Proc. Natl. Acad. Sci. (USA) 83:8923–8925.
Kashani–Sabet, M., et al. (1994) Cancer Res. 54:900–902.
Gottesman, M.M. (1993) Cancer Res. 53:747–754.
Ueda, K. et al. (1987) J. Biol. Chem. 262:17432–17436.
Teeter, L.D., et al. (1991) Cell Growth & Diff. 2:429–437.
Shen, D.W. et al. (1986) Science 232:643–645.
Cole, S.P.C. et al. (1992) Science 258:1650–1654.
Beck, W.T., et al. (1993) Adv. Enz. Reg. 33:113–127.

Primary Examiner—John L. LeGuyader
Attorney, Agent, or Firm—Rothwell, Figg, Ernst & Kurz, P.C.

[57] ABSTRACT

The effects of suppressing c-fos oncogene expression on drug or radiation resistant mammalian cells are described. A2780S human ovarian carcinoma cells with resistance to actinomycin D were isolated and the resultant A2780AD cells exhibited the MDR phenotype. A hammerhead ribozyme designed to cleave fos RNA cloned into the pMAMneo plasmid was transfected into A2780AD cells. Induction of the ribozyme resulted in decreased expression of c-fos, followed by that of mdr-1, c-jun, and p53. Reversal of the MDR phenotype by the anti-mdr ribozyme occurred one-fourth as rapidly as that induced by the anti-fos ribozyme. These studies demonstrate the primacy of the c-fos oncogene in maintaining the resistant phenotype in human cancer cells. Thus, down regulation of fos/jun will make resistant cancer cells more sensitive to conventional treatment, i.e., cancer chemotherapeutic agents and/or radiation.

8 Claims, 8 Drawing Sheets

MODULATION OF DRUG AND RADIATION RESISTANT GENES

This application is a 371 of PCT/US/9410215, filed Sep. 12, 1994.

TECHNICAL FIELD

This invention relates to the modulation of the drug resistant phenotype in mammalian, including human, cancer cells, which will make cancer cells sensitive to chemotherapy treatment and/or radiation treatment.

BACKGROUND OF THE INVENTION

Despite tremendous strides in understanding the molecular basis of cancer (1),[1] treatment of human cancer is still limited by the toxicity of chemotherapeutic agents and the development of intrinsic or acquired resistance to these drugs. Cis-diamminedichloroplatinum (II) (cisplatin) is one of the most widely-used anticancer agents, active in the treatment of ovarian, testicular, head-and-neck, non-small cell lung and brain tumors, among others (2). However, the rapid development of resistance to cisplatin represents an important challenge to clinicians and laboratory investigators alike. Therefore, understanding the biochemical and molecular basis of cisplatin resistance may potentially result in the development of rational approaches to circumvent this problem. At the core of understanding cisplatin resistance lies the realization of both the similarities and differences between the mechanisms of cisplatin action and resistance and that of other chemotherapeutic agents. Cisplatin-resistant cells display a unique cross-resistance pattern to multiple agents, including anti-metabolites such as 5'-fluorouracil and methotrexate, DNA polymerase inhibitors such as azidothymidine (AZT), and topoisomerase inhibitors such as camptothecin and etoposide. This "atypical" multidrug resistance is both phenotypically and molecularly distinct from the "classical" multidrug resistance which may involve overexpression of the MDR-1 gene (3).

[1] The bibliography precedes the claims.

A cursory review of the literature in cisplatin resistance quickly points to a potentially confusing array of mechanisms purported to be involved in this process, most of them seemingly disparate and unrelated. Recent advances in the workings of signal transduction in normal and cancer cells have led to a more cohesive picture of cellular pathways involved in the response to extracellular agents (e.g., growth factors, tumor promoters, viruses, and chemotherapeutic agents). This in turn has merged seemingly independent biochemical processes activated in response to various stimuli. An important molecular mechanism in cisplatin resistance concerns the c-fos proto-oncogene. The Fos protein dimerizes with the c-jun gene product to drive many important cell processes by transcriptional activation of AP-1-responsive genes (4). Numerous AP-1-responsive genes have been identified which participate in DNA synthesis and repair processes and which have been implicated in cisplatin resistance (5). These include metallothionein, DNA polymerase β, thymidylate synthase, topoisomerase II, and glutathione-S-transferase. Furthermore, the Fos/Jun heterodimers are thought to mediate the effects of H-ras activation following growth factor activation (6). And protein kinase C is a known participant in cellular signalling pathways leading to the activation of c-fos gene expression (4).

SUMMARY OF THE INVENTION

This invention elucidates signal transduction processes which mediate cellular response to extracellular agents. Common signalling pathways, e.g., those involving c-fos/c-jun become activated in response to diverse stimuli such as growth factors and chemotherapeutic agents. See FIGS. 2 and 3. The activation of the Fos/Jun complex in the nucleus, which typically occurs in a transient fashion, is a key feature of this response. These transient increases in gene expression then result (through transcriptional activation of AP-1responsive genes) in long term phenotypic changes. However, there is also specificity within the system. Therefore, Fos/Jun activation by cisplatin may lead to induction of genes involved in DNA synthesis and repair, metallothionein, and glutathione-S-transferase, whereas its activation by actinomycin D or etoposide, compounds known to be in the classical multidrug-resistant phenotype, may lead to induction of the mdr-1 and topoisomerase II genes. Thus, even though the cell uses similar nuclear oncoproteins to respond to different stimuli, it has the ability to differentiate between them by its differential activation of genes further downstream in the signal transduction cascade by selection pressure of the agent being used.

Pursuant to this invention, the MDR phenotype is mediated or reversed by inhibition of Fos/Jun expression with consequent down-regulation of AP-1-responsive genes downstream in the signal transduction pathway.

The invention also implicates ribozyme technology to uncouple downstream events following the administration of diverse chemotherapeutic agents. For example, an anti-fos ribozyme reverses the MDR phenotype while concurrently reducing expression of MDR-1, c-jun, p53 and topoisomerase I.

DETAILED DESCRIPTION OF THE INVENTION

Pursuant to the invention, the mdr-1 phenotype in mammalian, including human, cancer cells is mediated or reversed by the down-regulation of the Fos/Jun complex expression and by the suppression or deactivation of genes downstream from Fos/Jun in the signal. This will make cancer cells sensitive to chemotherapy treatment.

SIGNAL TRANSDUCTION PATHWAY

Figure 1:
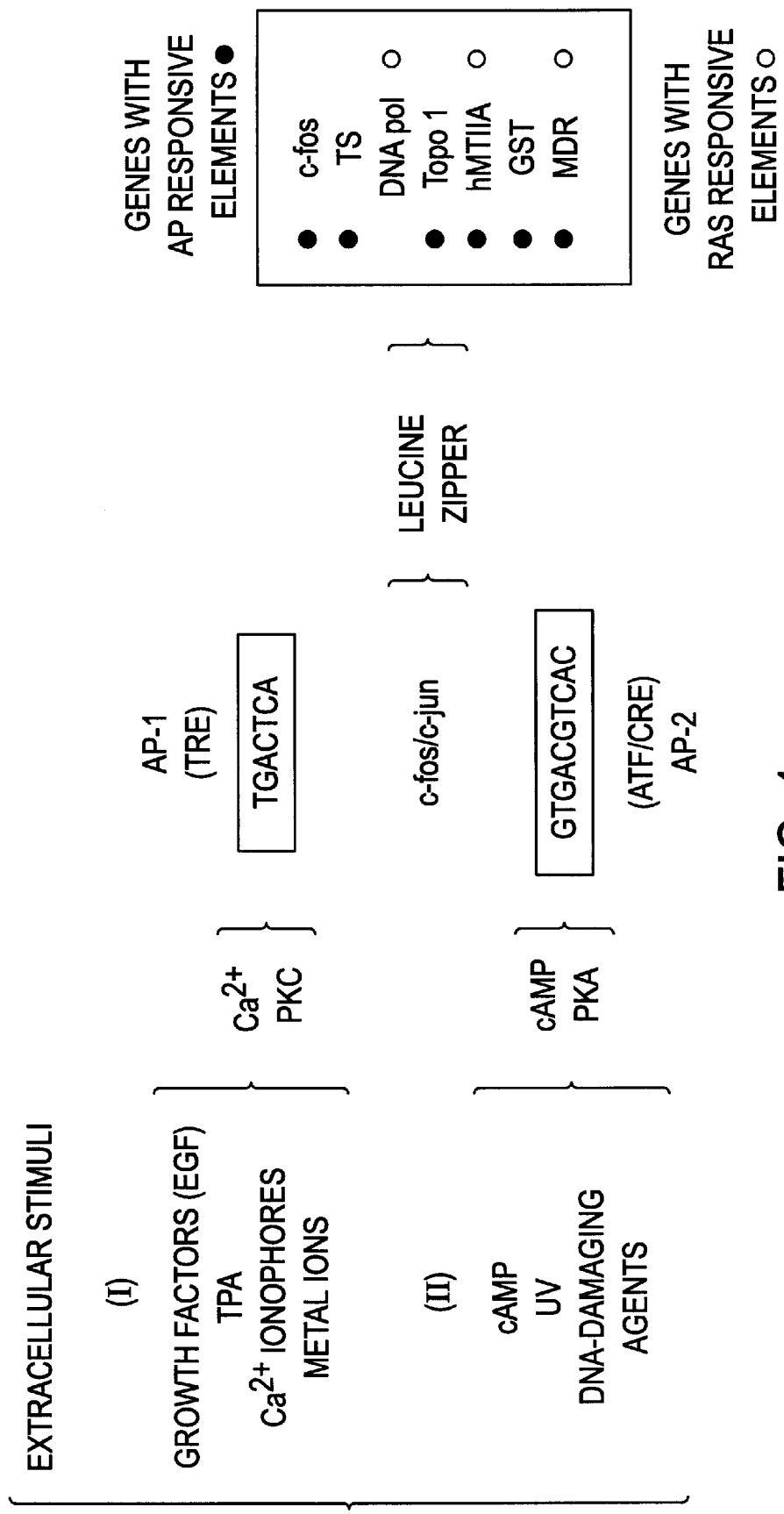
FIG. 1 is a schematic illustration of a signal transduction pathway and its involved components. The sequence GTGACGTCAC shown in this figure is SEQ ID NO:1.
Figure 2:
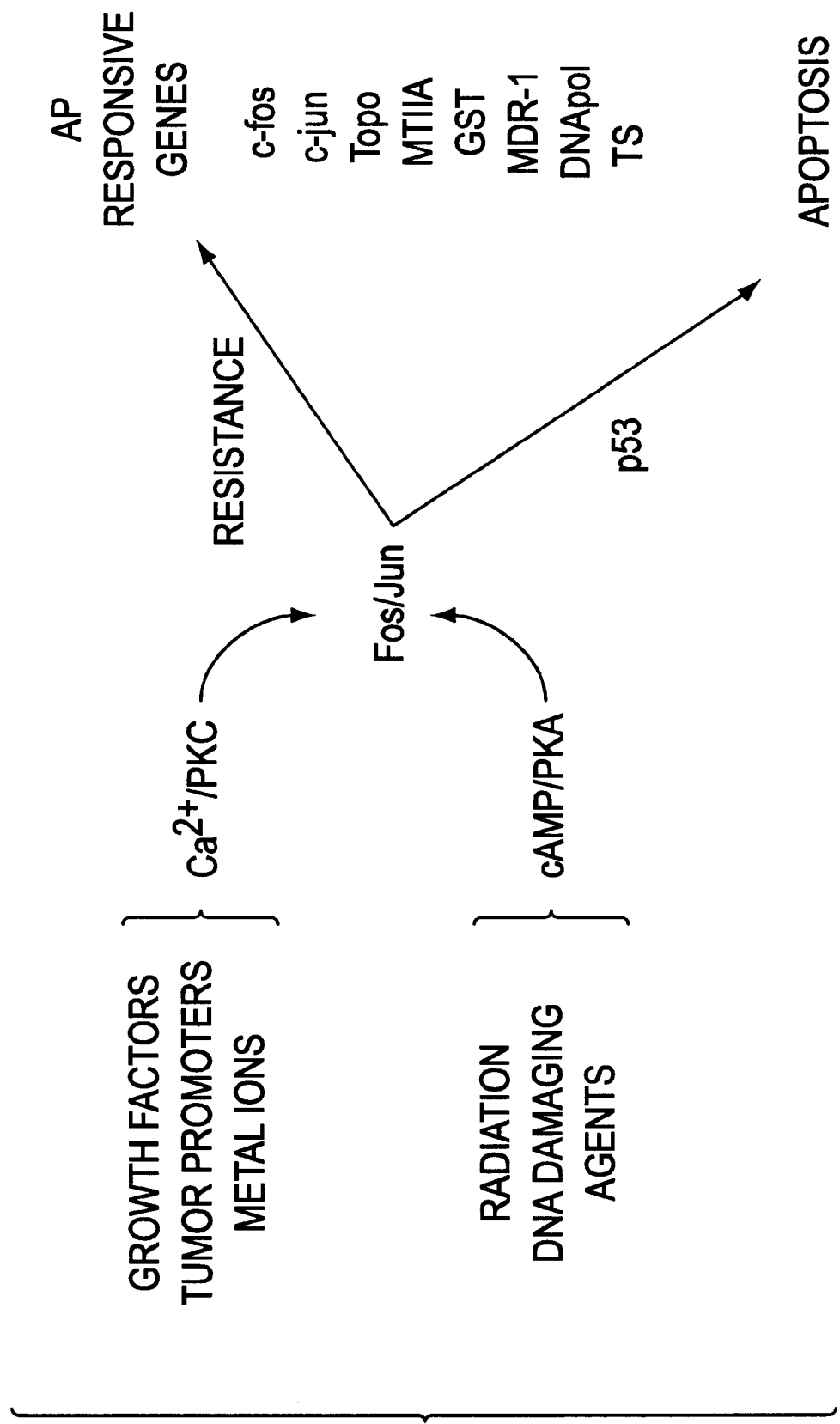
FIG. 2 is a schematic illustration of a mechanism of cancer cell drug resistance.
Figure 3:
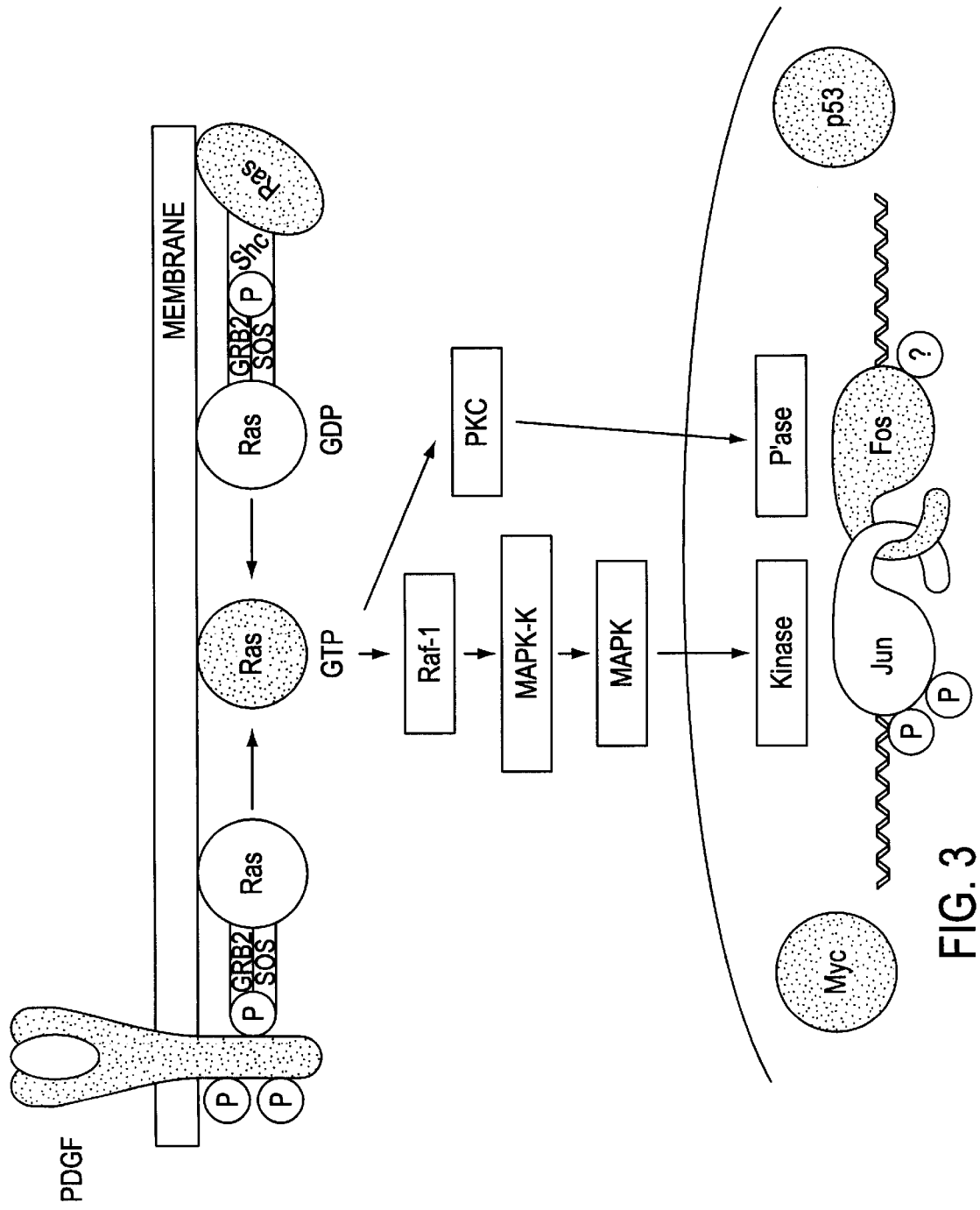
FIG. 3 is a schematic illustration taken from *Nature* 365:782 (1993) of a cascade activated by membrane tyrosine kinases associated with epidermal growth factors (EGF) or platelet derived growth factor (PDGF). As the figure shows, the cascade involves raf-1, MAP kinase kinase, and MAP kinase. MAP kinase translocates to the nucleus and may phosphorylate Jun and Fos proteins.

As FIGS. 1 and 2 show, membrane signal transduction includes two major pathways; the first is through protein kinase C (PKC), and the second is through cAMP and protein kinase A (PKA). Both PKC and PKA are followed by nuclear signaling through a phosphorylation cascade. PKC is activated by growth factors, such as epidermal growth factor (EGF) and platelet-derived growth factor (PDGF), and the tumor promoter 12-O-tetradecanoylphorbol-13-acetate (TPA). It has been reported that EGF increased cisplatin sensitivity in human ovarian carcinoma cell lines (7). The sensitization to cisplatin was shown to be dependent on both EGF concentration and EGF receptor number; the results suggested that the signal pathway activated by EGF determined the sensitivity of the cisplatin. A monoclonal antibody against the c-erbB-2 protein, a member of the EGF receptor family, also enhanced the cytotoxicity of cisplatin against a human breast cancer cell line (8). TPA is a dynamic modular of PKC. A PKC activator, bryostatin 1, sensitized human cervical carcinoma cells to cisplatin (9), possibly by increasing cellular accumulation of cisplatin. Meanwhile, several ligands such as prostaglandins stimulate adenyl cyclase, resulting in increased intracellular cAMP levels. The increased cAMP activates PKA. In one study, a relationship between cAMP and cisplatin uptake has been described (10). Cisplatin uptake was correlated to cAMP levels in the human ovarian cell carcinoma cell line, while the uptake was not associated with cAMP levels in the resistant cell subline to cisplatin. This study showed that the signal pathway through cAMP and PKA could be modulated to enhance sensitivity to cisplatin.

As FIG. 1 also shows, expression of cancer genes responsive to activator proteins is amplified by protein binder attachment, e.g., by leucine zipper, to a protein kinase mediated combination of an external stimulation and an activator protein sequence such as AP-1 or AP-2. Reaction of cisplatin with methionine yields Hras which amplifies the expression of Hras responsive cancer genes.

As FIG. 1 also shows, c-fos, TS, Topo-1 and GST are responsive to activator proteins (AP), DNA polymerase is responsive to Hras, and hMTIIA and MDR are responsive to both AP and Hras.

Protein promoter sequences, e.g., activator protein 1 (AP-1) and activator protein 2 (AP-2) genes were identified in 1987 (11, 12). Transcriptional selectivity of eukaryotic genes is mediated by complex control regions of promoter enhancer elements (12). AP-1, which stimulates transcription in vitro and binds specifically to the sequence TGACTCA in both the basal level enhancer (BLE) of HMTIIA and the 72 bp enhancer region of SV40, is described. It is suggested that AP-1 functions by interacting with a specific enhancer element and that its activation may be modulated by treatment of cells with tissue plasminogen activator (TPA) which stimulated protein kinase C (12).

It is also germane to the invention that gene regulation occurs by protein interaction as determined in the late 1980's (13, 14). It was found the expression of various genes that contain the AP-1 promoter sequence is enhanced when the promoter is bound to a leucine zipper Fos/Jun heterodimer (15, 16).

AP-1 plays an important role in RNA transcription. AP-1 is a complex of several different proteins, including the c-jun and c-fos proteins. c-jun expression was induced by treatment of human myeloid leukemia cells with cisplatin (17). The increased c-jun expression could be associated with the PKC-dependent pathway because down-regulation of PKC by TPA decreased the cisplatin-induced c-jun expression. The oncogene fos showed increased expression in cisplatin resistant cells and with cisplatin treatment in vitro (18, 19, 20) and in patients (18, 21). The c-fos oncogene has been shown to modulate the expression of AP-1 responsive genes such as dTMP synthase, topoisomerase I and metallothionein.

MECHANISM OF DRUG RESISTANCE

A mechanism of drug resistance is illustrated by FIG. 2. It outlines the signal transduction pathway from a point of view different from that shown by FIG. 1.

There have been a group of genes associated with drug resistance for cancer chemotherapy agents. The genes on the right-hand side of FIG. 2, fos, jun, etc., have all been identified over the past eight years to contain AP-1 responsive elements in their gene promoter region. These genes have all been identified as being up-regulated, over-expressed in tumor cells that are resistent to a wide spectrum of cancer chemotherapy agents. These genes are up-regulated because there is an increased amount of the proteins fos and jun. These two proteins bind to the AP-1 sequence on the drug resistant genes. fos and jun are over-expressed from stimulation by the protein kinase pathway. The protein kinase pathway is stimulated by the drugs interacting at the cell membrane.

In summary, cancer chemotherapy agents interact at the membrane, stimulate the protein kinase pathway, up-regulate the Fos/Jun complex which binds to the AP-1 binding sites on genes that will confer drug resistance to the tumor cells. Those genes are identified in the right-hand column of FIG. 2.

The p53 gene, which codes for a nuclear transcription factor, is known to play a crucial role in the regulation of DNA replication at the G1/S checkpoint (22, 23). Wild-type p53 allows cells to arrest in G1 so as to provide an opportunity for DNA repair prior to commencement of replicative DNA synthesis. In contrast, mutant p53 proteins are unable to act in this manner; p53 mutations are now believed to be a major cause of genetic instability in many cancers (24). Elevated p53 protein levels were observed in both A2780/cp70 and OVIP/DDP cisplatin-resistant ovarian human tumor lines. The A2780 cell line had a wild-type p53 gene, while the OVIP/DDP had a heterozygous mutation at codon 126 (25). These data suggested the close correlation between cisplatin resistance and DNA repair ability conferred by the function p53 protein.

The role of DNA polymerase β in the cell has been linked to DNA repair by gap-filling synthesis (26; see section entitled "Repair of Cisplatin-DNA Adducts"). DNA polymerase β, as well as metallothionein, has an Hras responsive element that responds to changes in Hras gene expression (27, 28). Some reports show a correlation between cisplatin resistance and Hras gene expression (29, 30). These studies have been confirmed in cisplatin-resistant human cells in vitro and from patients (31, 19, 21, 32). The Hras oncogene has also been shown to influence the methionine requirement in Hras transformed cells (33). These studies strengthen the link between methionine/folate metabolism, DNA repair systems and proto-oncogenes. Hras may also enhance transcriptional activity of c-jun through specific changes in the phosphorylation of the Jun protein (34).

Topoisomerase I and II are nuclear enzymes involved in various DNA transactions such as replication, transcription, and recombination (35, 36). The function of topoisomerase II is based on its ability to relax DNA in a two-step process involving the nicking and religation of both strands of the DNA double helix. Novobiocin, a topoisomerase II inhibitor, inhibited 73% of topoisomerase II activity in the nuclear extracts of HBT28 human glioblastoma cells; residual DNA crosslinking in the cells was increased by 3-fold in cells treated with cisplatin, compared with untreated cells (37). The data suggested that topoisomerase II could potentially affect the level of DNA interstrand crosslinks induced by cisplatin.

EXEMPLIFICATION OF THE INVENTION

Pursuant to this invention, drug resistance in mammalian, including human, cancer cells is reversed or ameliorated by the down-regulation of the expression of the Fos/Jun heterocomplex and of AP-responsive genes downstream from Fos/Jun in the transduction pathway. Reversal of the MDR phenotype by ribozyme suppression of c-fos oncogene expression illustrates one practical application of the invention. More particularly, this example indicates that reversal of the MDR phenotype occurs through a transcriptional cascade consequent from repression of c-fos gene expression.

MATERIALS AND METHODS

Genes. cDNAs were provided as follows: c-jun, Dr. R. Tjian (Berkeley, Calif.); p53 (php53c-1), Dr. M. Oren (Weizmann Institute, Israel) and human topoisomerase 1 (clone D1), Dr. L. Liu (Johns Hopkins Sch. of Medicine). Human c-fos (#41024) cDNA, human MDR-1 (#39839) cDNA and the pMMV-fos plasmid were obtained from American Type Culture Collection (Rockville, Md.). cDNAs were isolated as previously described (5). [$^3$H(G)] actinomycin D was obtained form Moravek (La Brea, Calif.).

A2780 Cells. The drug-sensitive human ovarian carcinoma cell line A2780S, was obtained from Dr. R. Ozols (Fox Chase Cancer Center), and the A2780AD-resistant cell line was isolated by weekly administrations of continuous exposure (for 72 hours) actinomycin D for nine months. In general, the cells were transferred to new RPMI-1640 medium on a weekly basis as described (5). The A2780AD cell line has a stable resistance to actinomycin D when grown in the absence of drug. For cytotoxicity determinations, 100 cells were inoculated in 60 mm tissue culture dishes. Twenty-four hours later, the cells were treated with cancer chemotherapeutic agents. The colonies were washed nine days later, fixed in methanol, stained with Giemsa dye and counted (38). A2780ADfosRz cells were pretreated with 0.5 μM dexamethasone for 24 hours prior to the addition of the chemotherapeutic agents (15). The $EC_{50}$ represents the drug concentration which inhibited 50% of the cell growth in the various cell lines.

Plasmid Construction. The anti-fos ribozyme was cloned into the plasmid pMAMneo (Clontech Lab, Palo Alto, Calif.) using two synthetic single-stranded oligodeoxyribonucleotides spanning a 53-base pair sequence with two flanking Bam HI restriction sites. Primers for screening cell lines for the presence of pMAMneofosRz plasmid were previously described (39).

The plasmid pHβAPr-1 neo (Phβ) was obtained from Dr. L. Kedes (USC, Los Angeles, Calif.). The anti-MDR ribozyme was prepared from two synthetic single-stranded oligodeoxyribonucleotides as previously described (40).

Transfection Studies. Subconfluently growing cells were transfected by electroporation according to a protocol provided by IBI (New Haven, Conn.). Cells were selected in growth medium containing 500 μg/ml geneticin (G418-sulfate, Gibco) for four weeks. Individual G418-resistant colonies were picked, grown and screened for expression of the anti-fos ribozyme. Reverse transcriptase (RT) PCR, utilized to detect ribozyme expression, was performed using 100 ng of mRNA from various A2780 cell lines, primers for synthesis of the ribozyme construct, and a protocol provided by Perkin-Elmer-Cetus. The amplification, blotting, and hybridization procedures were performed as described (39). The sequences for primers and the probe used to detect anti-fos ribozyme expression were previously published (5). The quantification of the RT-PCR assay was performed by the concurrent use of known mRNA quantities in the amplification reaction.

Northern Analysis. RNA isolation, electrophoresis, hybridization and densitometric analysis (Ambis) were performed as previously described (41).

Transport Studies. The uptake of radioactive [$^3$H] actinomycin D (5 μM, 150 μCi/mmol; dissolved in RPMI 1640 media without serum) into different A2780 cultured cell lines (60 mm diameter petri dishes) was measured as previously described (42). The uptake over a period of 120 minutes was quantified as follows: at each time point, cells were washed three times with ice-cold Dulbecco's phosphate-buffered saline (PBS, without $CaCl_2$ and $MgCl_2$, Gibco). The radioactive material associated with these cells was solubilized by incubating the cells overnight in 1 M NaOH. Aliquots were saved for protein determination, and the remainder was neutralized with 1 M HCl. The radioactivity was determined by scintillation spectrometry as previously described (42).

RESULTS

Figure 4:
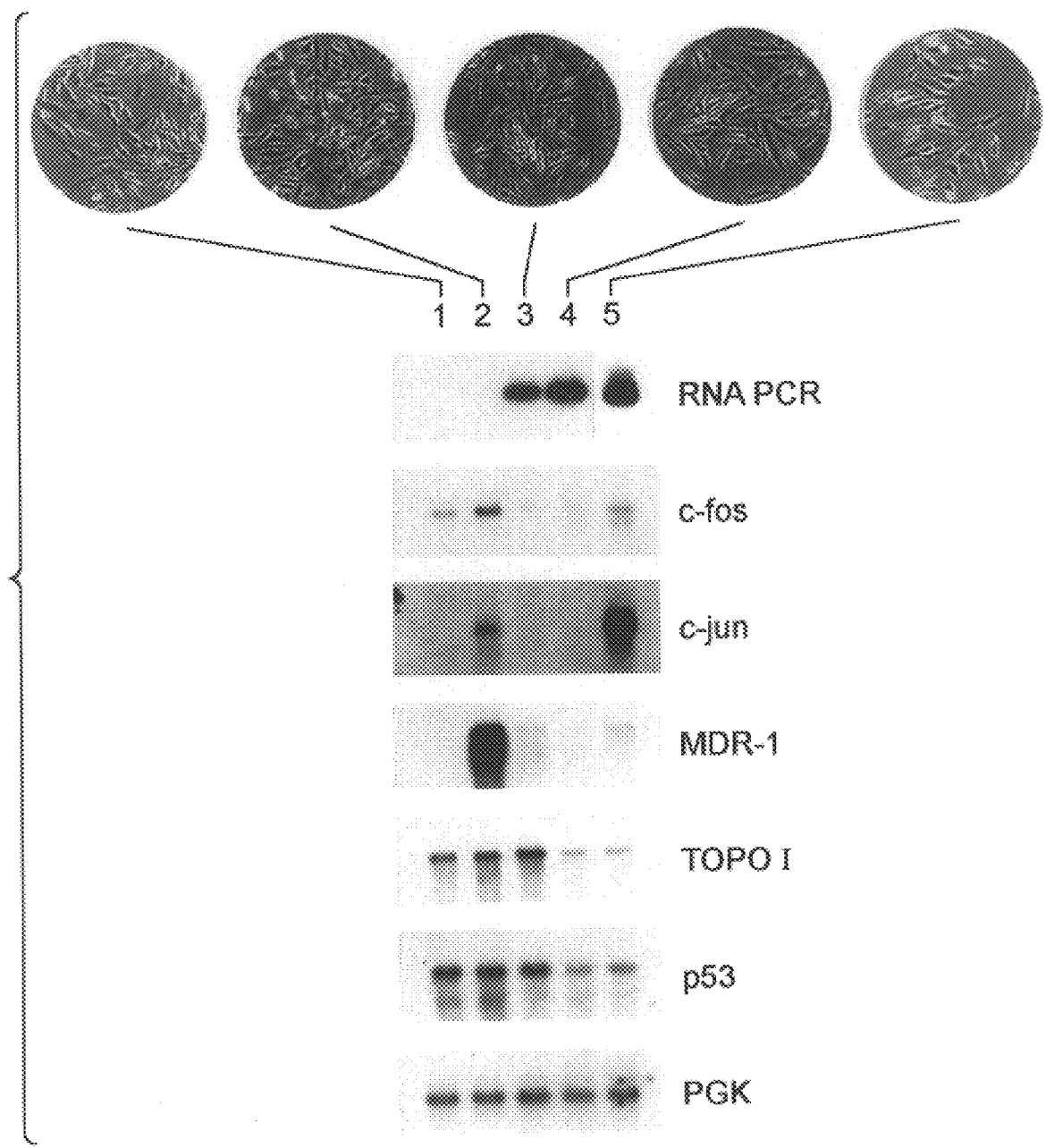
FIG. 4 depicts morphology and relevant gene expression in various A2780 cell lines. A2780S cells (lane 1), A2780AD cells (lane 2), A2780ADfosRZ-2 cells untreated (lane 3) and treated with dexamethasone for 24 hours (lane 4) and A2780ADmdrRz cells (lane 5) were analyzed by Northern blots with 2 μg mRNA in each lane. After RNA isolation and Northern blotting, gene expression of c-fos, c-jun, MDR-1, topoisomerase 1, mutant p53, and PGK was assayed using hybridization of the blot with labeled cDNA of each gene. Ribozyme RNA was detected by RT-PCR with 100 ng of mRNA.

Parental A2780S human ovarian carcinoma cells were grown in the presence of actinomycin D weekly for nine months, and the resultant subline (denoted A2780AD) was shown to be 16.6-fold more resistant to actinomycin D, with an $EC_{50}$ of 10.0 nM, than to A2780S cells $EC^{50}$ 0.6 nM, Table 1). A2780AD cells were demonstrated to exhibit the MDR phenotype, with cross-resistance to vincristine, doxorubicin, and VP-16 (Table 1). Associated with this resistance spectrum was a morphological change to cuboidal cells when compared to the spindle-shaped drug-sensitive A2780S cells (FIG. 4). There was no increased resistance to methotrexate, a drug not in the MDR family.

Expression of the MDR phenotype was concomitantly associated with overexpression of the mdr-1 gene (FIG. 4), without the presence of mdr-1 gene amplification (data not shown). Moreover, ($^3$H)-actinomycin D uptake was shown to be significantly reduced in A2780AD cells (FIG. 5), corresponding to overexpression of mdr-1, which encodes the P-glycoprotein efflux pump. A2780AD cells were studied for expression of genes previously implicated in signal transduction and drug resistance pathways. Interestingly, A2780AD cells also overexpressed the proto-oncogenes c-fos and c-jun, and, to a lesser degree, topoisomerase I and the mutant form of the tumor suppressor gene p53 (FIG. 4).

Elevated c-fos has been previously demonstrated in cisplatin-resistant cell lines (43), and expression of an anti-fos ribozyme reversed cisplatin resistance in A2780DDP cells (5). To investigate whether the anti-fos ribozyme could also modulate MDR, the dexamethasone-inducible plasmid pMAMneofosRz (5) containing the ribozyme was electroporated into A2780AD cells. Ten colonies were selected with resistance to G418, and five different clones were assayed and shown to express the anti-fos ribozyme and to have decreased c-fos mRNA (data not shown). Expression of the ribozyme in A2780ADpfosRz (clone 2) cells was demonstrated by RT-PCR (FIG. 4). Basal level c-fos expression was reduced to about 15% of control values in transformants (FIG. 4). After further induction of the ribozyme by dexamethasone administration in a time course assay, c-fos mRNA was maximally suppressed at 24 hrs (FIG. 4 and unpublished results). Fos protein expression was decreased in A2780ADpfosRz cells back to the sensitive level (data not shown). At the 24-hour time point, there was a concomitant decrease in expression of c-jun, mdr-1, topoisomerase I, and mutated p53 (FIG. 4). There was no significant change in expression of phosphoglycerate kinase in any of the cell lines or time points examined (FIG. 4 and unpublished results).

Morphologically, A2780ADpfosRz cells resembled the A2780S cells in appearance with elongated, spindly cells (FIG. 4). Pharmacologically, sensitivity to actinomycin D was completely restored by ribozyme activation in A2780ADpfosRz cells, with an EC$_{50}$ of 0.6 nM (Table 1). This was accompanied by reversal of resistance to other chemotherapeutic agents in the MDR phenotype, such as vincristine, doxorubicin, and VP-16 (Table 2). These results indicate that the anti-fos ribozyme reversed the MDR phenotype in A2780AD cells. Conversely, A2780S cells transfected with a vector containing the c-fos gene exhibited 13.0-fold greater resistance to actinomycin D (Table 1) and cross-resistance to agents in the MDR family (A2780SpMMVfos cells, Table 2). As controls, A2780AD cells transfected with the pMAMneo vector only and the anti-fos ribozyme in the reverse orientation (RfosRz) showed little change in resistance to actinomycin D (Table 2). Furthermore, 0.5 μM dexamethasone administered to A2780AD had no significant effects on actinomycin D cytotoxicity in A2780AD cells (Table 1).

TABLE 1

ACTINOMYCIN D CYTOTOXICITY IN A2780 CELL LINES

| CELL LINE | EC$_{50}$(nM) |
| --- | --- |
| A2780S | 0.6 |
| A2780AD | 10.0 |
| A2780AD (+dex) | 8.5 |
| A2780SpMMvfos | 7.8 |

TABLE 1-continued

ACTINOMYCIN D CYTOTOXICITY IN A2780 CELL LINES

| CELL LINE | EC$_{50}$(nM) |
| --- | --- |
| A2780ADpMAMneo (vector only) | 9.6 |
| A2780ADpfosRz (no dex) | 0.8 |
| A2780ADpfosRz (+dex) | 0.6 |
| A2780ADpRfosRz | 6.6 |
| A2780ADpHβ (vector only) | 7.8 |
| A2780ADpMDRRz | 0.9 |

A2780 cells were plated and after 24 hrs were treated with six different concentrations of actinomycin D by continuous exposure for 72 hrs. 0.5 μM dexamethasone was administered as indicated (+ dex) to cells for 24 hrs prior to drug treatment. A2780ADpHβ cells contained the pHβApr-1 neo plasmid, without the ribozyme sequences. A2780ADpRfosRz denotes cells transfected with a plasmid containing the anti-fos ribozyme in the reverse orientation. The results are a mean of triplicate sets of experiments.

Figure 5:
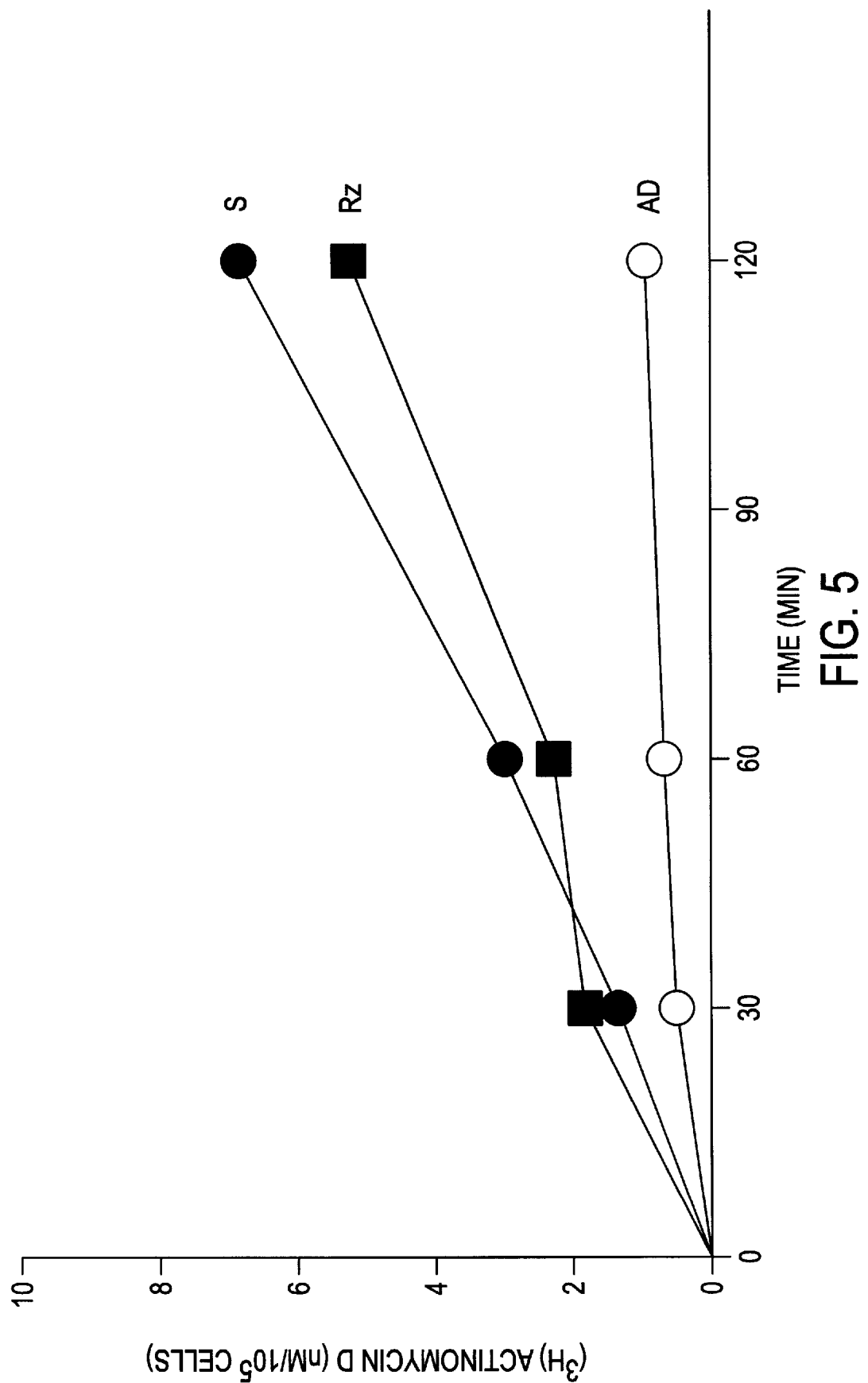
FIG. 5 illustrates the uptake of labeled actinomycin D into A2780 cells. A2780S, A2780D, A2780ADmdrRz cells were incubated with ($^3$H) actinomycin D (1 μM) over two hours. At 30, 60 and 120 minutes, samples of labelled A2780 cells were analyzed for radioactivity. See Methods for details.
Figure 6A:
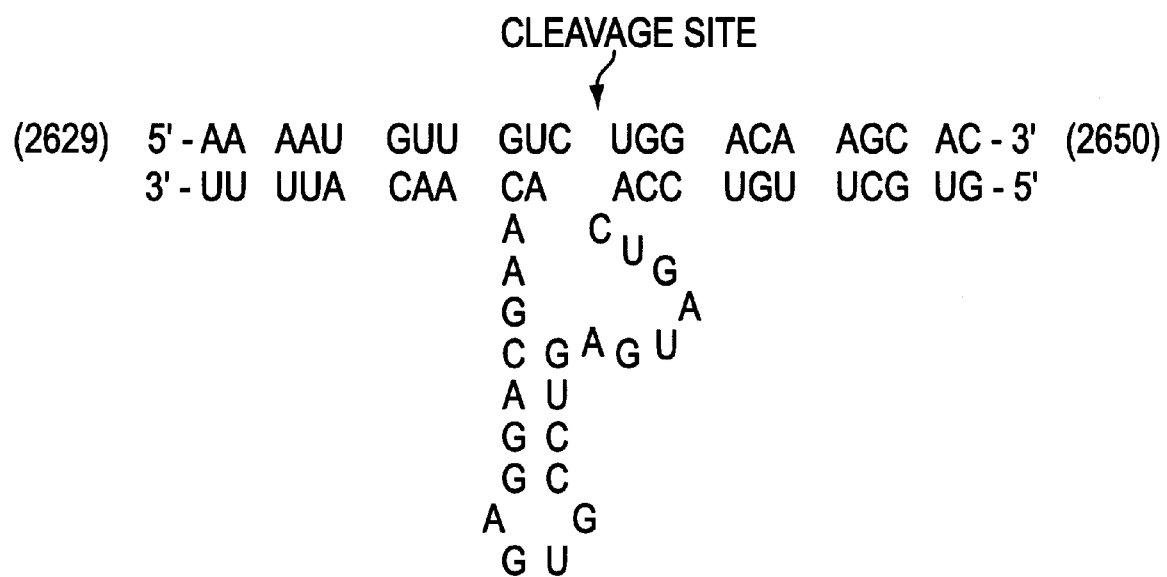
FIG. 6A depicts the relevant sequences of the MDR-1 gene containing the cleavage site at position 2639, as well as the sequence encoding the anti-MDR ribozyme. The upper strand is SEQ ID NO:2 and the lower strand is SEQ ID NO:3.
Figure 6B:
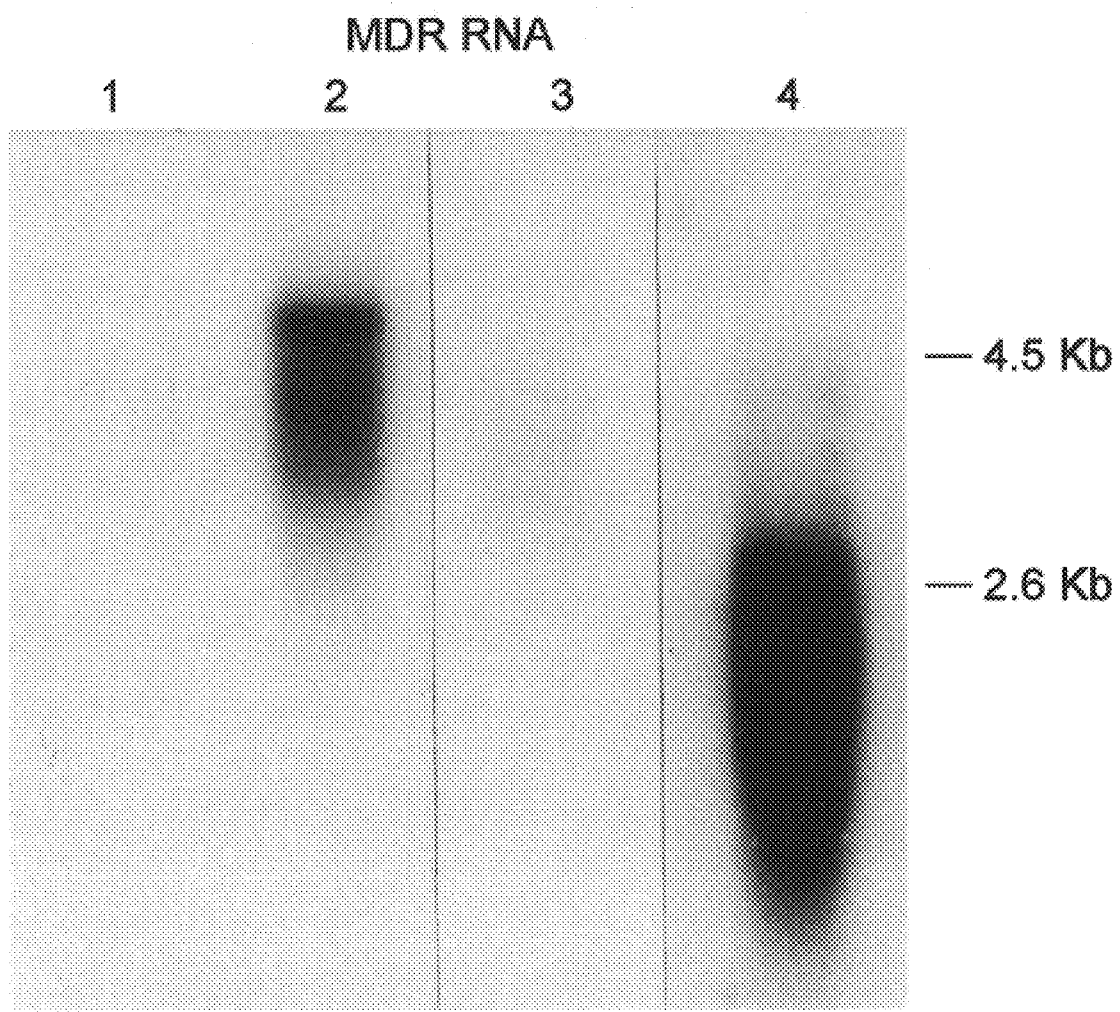
FIG. 6B shows cellular ribozyme cleavage of MDR-1 RNA. mRNA was isolated from A2780S (lane 1, 2 μg), A2780AD (lane 2, 2 μg), A2780AD mdrRz (lane 3, 2 μg) and A2780ADmdrRz cells (lane 4, 10 μg) and hybridized to labeled MDR-1 cDNA.

Next, the effects of inhibiting mdr-1 gene expression on the MDR phenotype were investigated. To this end, the A2780AD cells were transfected with the pHβmdrRz plasmid containing the β-actin gene promoter and encoding a ribozyme previously designed and demonstrated to cleave the GUC sequence at codon 880 of exon 21 of mdr-1 mRNA (P. Holm et al., manuscript submitted; FIG. 6A). This target site resides between two ATP-binding sites, with possibly important implications for P-glycoprotein function (44). The resultant A2780ADpmdrRz cells were shown to express the anti-mdr ribozyme by RT-PCR (FIG. 4). Mdr-1 gene expression was reduced over 90% in A2780ADpmdrRz cells when compared to A2780AD cells (FIG. 4). Demonstration of ribozyme cleavage was achieved by Northern analysis of mdr-1 polyadenylated mRNA (FIG. 6B). In FIG. 6B, using 2 μg of cellular mRNA and labeled mdr-1 cDNA, only the full length mdr-1 transcript (4.5 kb) was detected in A2780AD cells (lane 2). In A2780ADpmdrRz cells (lane 3), no mdr-1 transcript was detected in 2 μg of mRNA. Using 10 μg of mRNA, however, a strong band was detected beginning at 2.6 kb, the approximate length of the mdr-1 transcript after ribozyme cleavage (FIG. 6). After several weeks of in vitro propagation, the anti-mdr ribozyme restored actinomycin D cytotoxicity, with an EC$_{50}$ of 0.9 nM (Table 1). In contrast, there was no change in the EC$_{50}$ of actinomycin D in A2780AD cells transfected with the pHβApr-1 neo vector only (Table 1, pHβ). Morphologically, A2780ADpmdrRz cells had the spindly appearance of A2780S cells (FIG. 4). Concomitantly, labeled actinomycin D uptake was present at levels similar to that of A2780S cells (FIG. 5). The resistance panel to other agents in the MDR phenotype was significantly altered in a manner similar to that of the A2780ADpfosRz cells, with near-complete restoration of sensitivity to vincristine, doxorubicin, and VP-16 (Table 2). There was no change in the EC$_{50}$ of methotrexate in these studies (Table 2).

TABLE 2

Drug Cytotoxicity in A2780 Cell Lines

| AGENT* | S | AD | SpMMVfos | EC$_{50}$ ADpfos-Rz −Dex | ADpfos-Rz +Dex | ADpMDR-Rz |
|---|---|---|---|---|---|---|
| VCR | 4.6 | 119.0 | 6.6 | 16.0 | 8.2 | 8.0 |
| Doxorubicin | 30.0 | 110.0 | 120 | 50.0 | 50.0 | 42.0 |
| VP-16 | 0.18 | 1.2 | 0.35 | 0.46 | 0.3 | 0.4 |
| MTX | 0.3 | 0.4 | n.d. | 0.3 | 0.4 | 0.4 |

A2780 cells were plated and 24 hrs later treated with VP-16 or doxorubicin or vincristine (VCR) for a continuous exposure or methotrexate (MTX) for a 2 hr exposure. The plates were stained six days later as described in Materials and Methods. Dexamethasone (0.5 µM) was administered to the A2780ADpfosRz cells for 24 hrs prior to drug treatment (+dex).
*All values are in nanomolar (nM) except for methotrexate which is in micromolar (µM)
n.d. denotes not done.

Finally, Northern analysis revealed decreased mRNA for c-fos and p53 (but not c-jun) in A2780ADpmdrRz cells when compared to drug-resistant A2780AD cells (FIG. 1).

Figure 7:
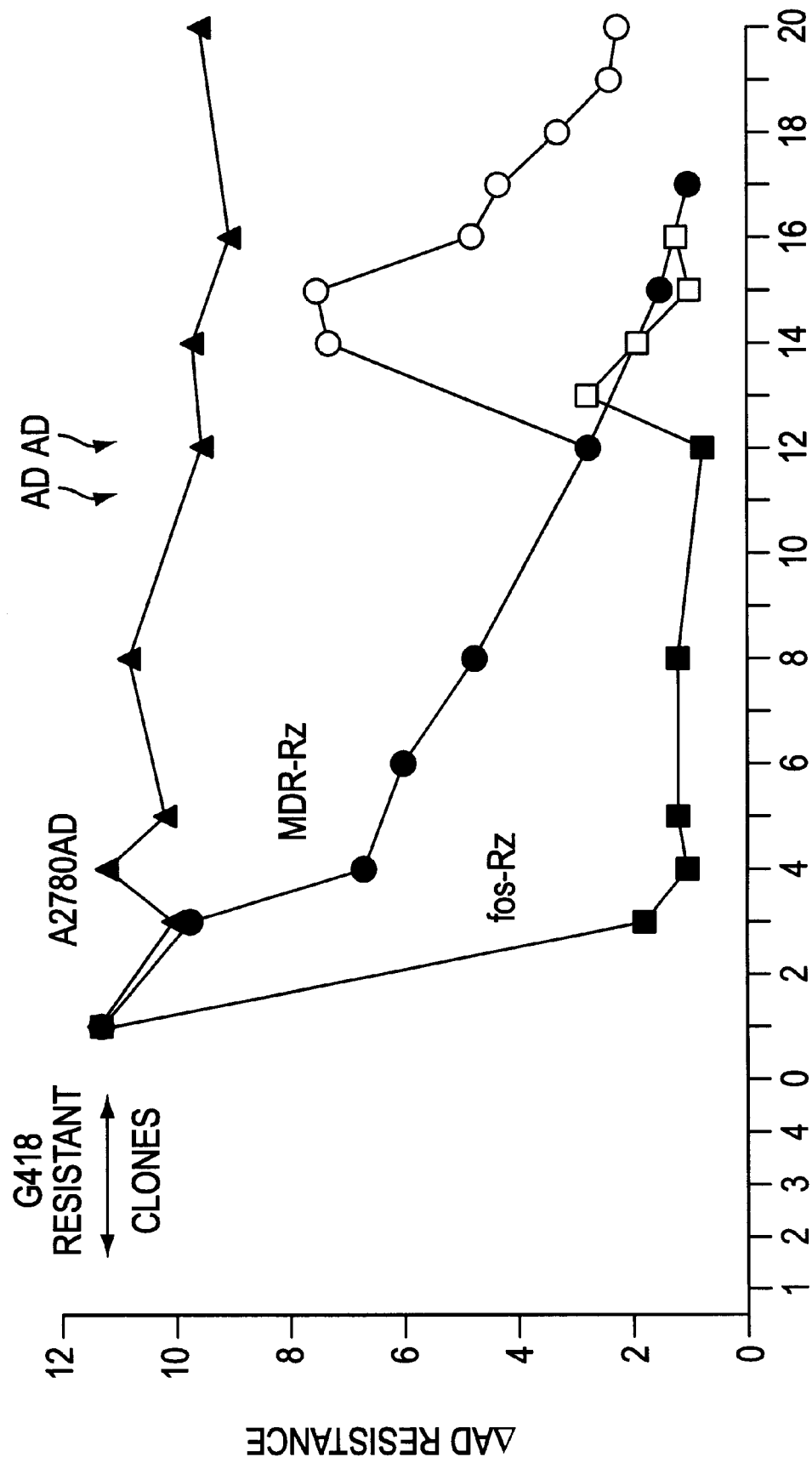
FIG. 7 depicts the changes in actinomycin D cytotoxicity in A2780AD cells. A2780 cell lines containing either the anti-fos ribozyme or the anti-MDR ribozyme were treated with actinomycin D weekly to monitor their level of drug sensitivity. At week 11 and week 12, the ribozyme-containing cells were rechallenged with actinomycin D. A2780AD cells were not treated with actinomycin D for a five month period as a control. These results represent a mean of three different clones assayed for actinomycin D cytotoxicity over 12 months.

In comparing the effects of the two ribozymes, a disparate pattern of resensitization to chemotherapeutic agents was observed upon plasmid transfection. The anti-fos ribozyme restored sensitivity to actinomycin D within three weeks after withdrawal of G418 (FIG. 7). In contrast, A2780ADpmdrRz cells initially were resistant to actinomycin D. After 17 weeks of propagation in culture, the EC$_{50}$ gradually reached sensitive levels, similar to that seen in A2780ADpfosRz cells. When the sublines were retreated with actinomycin D weekly for two weeks, A2780ADpfosRz cells were 3-fold more resistant to actinomycin D, and the EC$_{50}$ returned to baseline in three weeks. In A2780ADpmdrRz cells, however, the drug rechallenge resulted in an 8-fold increased resistance. This resistance decreased more slowly than in A2780ADfosRz cells, such that by week 20 a 4-fold level of resistance still remained (FIG. 7). As a control, A2780AD cells had a stable resistance to actinomycin D over a five-month period (FIG. 7).

These results illuminate the role of the c-fos gene in drug resistance by demonstrating that (i) cells expressing the MDR phenotype overexpress c-fos; (ii) cells transfected with and overexpressing c-fos exhibit MDR; and (iii) an anti-fos ribozyme reversed the MDR phenotype in A2780AD cells. The data utilized morphological, pharmacological, and molecular analysis to better define this association. Fos has been previously shown to play a role in resistance to agents not within the MDR family, such as cisplatin, AZT and 5-fluorouracil (15). Taken together, these studies indicate an expanded and more significant role for overexpression of c-fos in resistance to many of the different chemotherapeutic agents currently in use. Moreover, these results are instructive with respect to the acquisition of drug-resistance in oncogene-transformed cancer cells. The data suggest that fos mediates some of these effects through transcriptional activation of AP-1 responsive genes, such as MDR-1, topoisomerase I, metallothionein IIA and thymidylate synthase. The observation that c-jun expression is also decreased in A2780ADppfosRz cells supports the hypothesis that the aforementioned effects may occur through fos/jun interaction. The experimental results indicate that activation of this transcriptional cascade is important in MDR because anti-fos ribozyme action diminished downstream gene expression at 24 hours, the time point at which EC$_{50}$s were measured.

Expression of MDR-1 has been previously demonstrated to be modulated by the H-ras and p53 genes in chloramphenicol acetyl transferase (CAT) assays (25,26). These studies used co-transfection assays with the downstream promoter cloned into the CAT-containing vector in order to assess promoter responsiveness to these genes. In contrast, this application describes the analysis of gene expression in a cellular environment and in a time-dependent fashion after ribozyme induction by dexamethasone. These results support the previous finding linking mutant p53 expression with that of MDR-1. They extend that concept by demonstrating that diminished p53 and MDR-1 mRNA after anti-fos ribozyme action may contribute to reversal of the MDR phenotype. These studies also suggest an association between expression of c-fos and p53. Moreover, a putative connection exists in signal transduction between H-ras and c-fos, as fos antisense has been shown to abrogate H-ras-mediated activation of other genes such as collagenase and transin (27,28). Intriguingly, H-ras gene expression was also reduced in anti-fosRz treated cells (data not shown). Finally, c-jun expression is also linked to H-ras-directed pathways, as the H-ras gene product potentiates c-jun activity by phosphorylating jun (34). Collectively, these observations describe the existence of an intricate cellular network of cross-signalling involving transcriptional and post-translational regulation. These pathways appear to be activated in response to a diverse array of stimuli, such as growth factors, tumor promoters and cancer chemotherapeutic agents.

As mentioned earlier, the upstream regulatory sequences of the MDR-1 gene contain an AP-1 binding site (45). Even though this region is not the dominant promoter for mdr-1 in all circumstances, it has been shown to be required for full promoter activity in Chinese hamster ovary cells (46). In addition, the AP-1 containing promoter may be active in cell lines which overexpress mdr-1 RNA without gene amplification (44, 47), which is precisely the situation encountered in A2780AD cells. Therefore, down-regulation of mdr-1 RNA after anti-fos ribozyme action is part of the cascade effecting reversal of the MDR phenotype.

The results reported in this application also indicate the efficacy of an anti-mdr ribozyme in reversing the MDR phenotype. This parallels the use of anti-mdr ribozymes to suppress mdr-1 mRNA in other model systems. With extremely high levels of drug resistance, other mechanisms of resistance may be activated and may even predominate. It would be intriguing to use the anti-fos ribozyme in cell lines in which suppressing mdr-1 expression is insufficient to restore drug cytotoxicity or in which MRP (multi-drug resistant-related protein) is overexpressed (48).

A2780ADpmdrRz cells also displayed diminished gene expression of c-fos, topoisomerase I, and p53 (FIG. 4).

However, it must be noted that those experiments represent a one-time measurement, since the pHβApr1neo plasmid containing the anti-mdr ribozyme uses the β-actin promoter to drive constitutive expression of the ribozyme and is not inducer driven as shown with A2780ADpfosRz cells. Therefore, the reduced gene expression observed may be less a result of direct effects on transcriptional regulation of these genes and more a reflection of selection pressures on a cell subline displaying the drug-sensitive phenotype and containing normal levels of the mdr-1 gene product.

Finally, the differential pattern of drug sensitivity between the two ribozymes may offer mechanistic explanations for action of the two genes in drug resistance. The observation that the anti-fos ribozyme reversed actinomycin D resistance more quickly may suggest that c-fos may modulate genes other than mdr-1 which also contribute to the MDR phenotype. One such candidate is topoisomerase I, also implicated in atypical MDR, in which mdr-1 gene expression is unperturbed (49). The experiments described herein demonstrate that anti-fos ribozyme action has also resulted in reduced expression of topoisomerase I.

In conclusion, the data presented here demonstrate the efficacy of an anti-fos ribozyme in reversing the MDR phenotype, while reducing expression of mdr-1, c-jun, p53 and topoisomerase I. The anti-fos ribozyme was equally, if not more, effective than the anti-mdr ribozyme. This suggests the primacy of c-fos in drug resistance processes.

Thus, downregulation of c-fos will make tumor cells resistant to conventional treatment, more sensitive to this strategy of cancer chemotherapeutic agents and/or radiation treatment.

BIBLIOGRAPHY

1. Weinberg, R. A. (1989) *Cancer Res.* 49:3713–3721.
2. Rosenberg, B. (1985) *Cancer* 55:2303–2316.
3. Gottesman, M. M. (1993) *Ann.Rev.Biochem.* 62:385–427.
4. Ransone, L. J. & Verma, I. M. (1990) *Ann. Rev. Cell Biol.* 6:539–557.
5. Scanlon, K. J., Jiao, L., Funato, T., Wang, W., Tone, T., Rossi, J. J., & Kashani-Sabet, M. (1991) *Proc. Natl. Acad. Sci. (USA)* 88:10591–10595.
6. Boguski, M. S., McCormick F. (1993) *Nature* 366:643–654.
7. Christen, R. D., Hom, D. K., Porter, D. C., Andrews, P. A. (1990) *J.Clin.Invest.* 86:1632–1640.
8. Hancock, M. C., Langton, B. C., Than, T., Toy, P., Monhahan, J. J., Mischak, R. P., Shawver, L. K. (1991) *Cancer Res.* 51:4575–4580.
9. Basu, A., Lazo, J. S. (1992) *Cancer Res.* 52:3119–3124.
10. Mann, S. C., Andrews, P. A., Howell, S. B. (1991) *Int.J.Cancer* 48:866–872.
11. Marx (1987) *Science* 237:854–856 (1987).
12. Lee, et al. (1987) *Cell* 49:741–752.
13. McKnight (1991) *Scientific American*, pp. 54–64.
14. Abate, et al. (1990) *Proc.Natl.Acad.Sci.USA* 87:1032–1036 (1990).
15. Ransone, et al. (1989) *Int.J.Cancer* Supplement 4:10–21.
16. Kouzarides, et al. (1989) *Cancer Cells* 1:71–76.
17. Rubin, E., Kharbanda, S., Gunji, H., Weichselbaum, R., Kufe, D. (1992) *Cancer Res.* 52:878–882.
18. Scanlon, K. J., Lu, Y., Kashani-Sabet, M., Ma Jx, Newman, E. (1988) *Adv.Exp.Med.Biol.* 244:127–135.
19. Scanlon, K. J., Kashani-Sabet, M., Sowers, L. C. (1989) *Cancer Comm.* 1:269–275.
20. Hollander, M. C., Fornace, A. J. Jr. (1989) *Cancer Res.* 49:1687–1692.
21. Scanlon, K. J., Kashani-Sabet M., Miyaschi, H., Sowers, L. C., Rossi, J. J. (1989) *Anticancer Res.* 9:1301–1312.
22. Kastan, M. B., Onyekwere, O., Sidransky, D., Vogelstein, B., Craig, R. W. (1991) *Cancer Res.* 51:6304–6311.
23. Kuerbits, S. J., Plunkett, B. S., Walsh, W. V., Kastan, M. B. (1992) *Proc.Natl.Acad.Sci.USA* 89:7491–7495.
24. Raycroft, L., Wu, H. Y., Lozano, G. (1990) *Science* 249:1049–1051.
25. Brown, R., Clugston, C., Burns, P., Edlin, A., Basey, P., Vojtesek, G., Kay, S. B. (1993) *Int.J.Cancer* 55:678–684.
26. Wang, TS-F (1991) *Ann.Rev.Biochem.* 60:513–552.
27. Schmidt, C. J., Hamer, D. H. (1986) *Proc.Natl.Acad.Sci.USA* 83:3346–3360.
28. Kedar, P. S., Lowy, D. R., Widen, S. G., Wilson, S. H. (1990) *Mol.Cell.Biol.* 10:3852–3856.
29. Sklar, M. D. (1988) *Cancer Res.* 48:793–737.
30. Niimi, S., Nakagawa, K., Yokota, J., Tsunokawa, Y., Nishio, K., Terashima, Y., Shibuya, M., Terada, M., Saijo, N. (1991) *Br.J.Cancer* 63:237–241.
31. Scanlon, K. J., Kashani-Sabet, M. (1989) *J.Clin.Lab.Anal.* 3:323–329.
32. Kashani-Sabet, M., Lu, Y., Leong, L., Haedicke, K., Scanlon, K. J. (1990) *Eur.J.Cancer* 26:383–390.
33. Vanhamme, L., Szpirer C. (1987) *Exp.Cell Res.* 169:120–126.
34. Binetruy, B. Smeal, T., & Karin, M. (1991) *Nature* 351:122–127.
35. Wang, J. C. (1985) *Ann.Rev.Biochem.* 54:665–667.
36. Liu, L. F. (1989) *Ann.Rev.Biochem.* 58:351–375.
37. Ali-Osman, F., Berger, M. S., Rajagopal, B. S., Spence, A., Livingston, R. B. (1993) *Cancer Res.* 53:5663–5668.
38. Scanlon, K. J. & Kashani-Sabet, M. (1988) *Proc. Natl. Acad. Sci. (USA)* 85:650–653.
39. Kashani-Sabet, M., Funato, T., Tone, T., Jiao, L., Wang, W., Yoshida, E., Kashfian, B. I., Shitara, T., Wu, A. M., Moreno, J. G., Traweek. S. T., Ahlering, T. E. & Scanlon, K. J. (1992) *Antisense Res. Dev.* 2:3–15.
40. Sarver, N., Cantin, E. M., Chang, P. S., Zaia, J. A., Ladne, P. A., Stephens, D. A. & Rossi, J. J. (1990) *Science* 247:1222–1225.
41. Kashani-Sabet, M., Wang, W. & Scanlon, K. J. (1990) *J. Biol. Chem.* 265:11285–11288.
42. Scanlon, K. J., Newman, E. M., Lu, Y., & Priest, D. G. (1986) *Proc. Natl. Acad. Sci. (USA)* 83:8923–8925.
43. Kashani-Sabet, M., Funato, T., Florenes, V. A., Fodstad, O., & Scanlon, K. J. (1994) *Cancer Res.* 54:900–902.
44. Gottesman, M. M. (1993) *Cancer Res.* 53:747–754.
45. Ueda, K., Pastan, I., & Gottesman, M. M. (1987) *J. Biol. Chem.* 262:17432–17436.
46. Teeter, L. D., Eckersberg, T., Tsai, Y. & Kuo, M. T. (1991) *Cell Growth & Diff.* 2:429–437.
47. Shen, D. W., Fojo, A., Chin, J. E., Roninson, I. B., Richert, N., Pastan, I., & Gottesman, M. M. (1986) *Science* 232:643–645.
48. Cole, S. P. C., Bhardwaj, G., Gerlach, J. H., Mackie, J. E., Grant, C. E., Almquist, K. C., Steward, A. J., Kurz, E. U., Duncan, A. M. V., & Deeley, R. G. (1992) *Science* 258:1650–1654.
49. Beck, W. T., Danks, M. K., Wolverton, Kim, R., & Chen, M. (1993) *Adv. Enz. Reg.* 33:113–127.

---

I claim:

1. A nucleic acid encoding a ribozyme wherein said ribozyme has a sequence as set forth in SEQ ID NO:3.

2. An expression vector comprising the nucleic acid of claim 1.

3. The expression vector of claim 2 wherein said expression vector comprises plasmid pHβAPr-1 neo.

4. A cell transformed with the expression vector of claim 2.

5. The cell of claim 4 further comprising a vector encoding a fos ribozyme.

6. A nucleic acid comprising SEQ ID NO:3.

7. The nucleic acid of claim 6 wherein said nucleic acid is a ribozyme.

8. A cell which expresses the ribozyme of claim 7.

* * * * *

SEQUENCE LISTING (1) GENERAL INFORMATION:

(iii) NUMBER OF SEQUENCES: 3

(2) INFORMATION FOR SEQ ID NO:1:

(i) SEQUENCE CHARACTERISTICS:
       (A) LENGTH: 10 base pairs
       (B) TYPE: nucleic acid
       (C) STRANDEDNESS: double
       (D) TOPOLOGY: linear (ii) MOLECULE TYPE: DNA (genomic)

(iii) HYPOTHETICAL: NO (xi) SEQUENCE DESCRIPTION: SEQ ID NO:1:

GTGACGTCAC                                                                10

(2) INFORMATION FOR SEQ ID NO:2:

(i) SEQUENCE CHARACTERISTICS:
       (A) LENGTH: 22 base pairs
       (B) TYPE: nucleic acid
       (C) STRANDEDNESS: single
       (D) TOPOLOGY: linear (ii) MOLECULE TYPE: RNA (genomic)

(xi) SEQUENCE DESCRIPTION: SEQ ID NO:2:

AAAAUGUUGU CUGGACAAGC AC                                                  22

(2) INFORMATION FOR SEQ ID NO:3:

(i) SEQUENCE CHARACTERISTICS:
       (A) LENGTH: 43 base pairs
       (B) TYPE: nucleic acid
       (C) STRANDEDNESS: single
       (D) TOPOLOGY: linear (ii) MOLECULE TYPE: other nucleic acid
       (A) DESCRIPTION: /desc = "Ribozyme"

(xi) SEQUENCE DESCRIPTION: SEQ ID NO:3:

GUGCUUGUCC ACUGAUGAGU CCGUGAGGAC GAAACAACAU UUU                           43